United States Patent [19]

Yeh et al.

[11] 4,014,867

[45] Mar. 29, 1977

[54] PRODUCTION OF HEXAMETHYLENEIMINE FROM CAPROLACTAM

[75] Inventors: Chuen Y. Yeh, Succasunna; Harry E. Ulmer, Morristown, both of N.J.

[73] Assignee: Allied Chemical Corporation, Morris Township, N.J.

[22] Filed: Sept. 23, 1975

[21] Appl. No.: 616,105

[52] U.S. Cl. .................................... 260/239 B
[51] Int. Cl.$^2$ ............................... C07D 295/02
[58] Field of Search ......................... 260/239 B

[56] References Cited

UNITED STATES PATENTS

| 2,181,140 | 11/1939 | Lazier et al. | 260/583 |
| 2,187,745 | 1/1940 | Lazier et al. | 260/239 B |
| 2,223,303 | 11/1940 | Lazier et al. | 260/239 B |
| 2,232,059 | 2/1941 | Farlow | 260/239 B |

*Primary Examiner*—Donald G. Daus
*Assistant Examiner*—Mark L. Berch
*Attorney, Agent, or Firm*—Roger H. Criss; M. S. Jarosz

[57] ABSTRACT

A method of preparing hexamethyleneimine which comprises the steps of:

a. forming a solution of ε-caprolactam in a solvent selected from the group consisting of linear and cyclic ethers and polyethers having a boiling point of at least about 100° C, said solution having a concentration of about 1 to 40 percent by weight;

b. contacting said solution with gaseous hydrogen in the presence of a catalyst comprising copper chromite and at a temperature of about 150 to 300° C. and a pressure of at least about 1,000 psig, whereby a solution containing hexamethyleneimine is formed; and c. recovering hexamethyleneimine from said hexamethyleneimine-containing solution.

20 Claims, 1 Drawing Figure

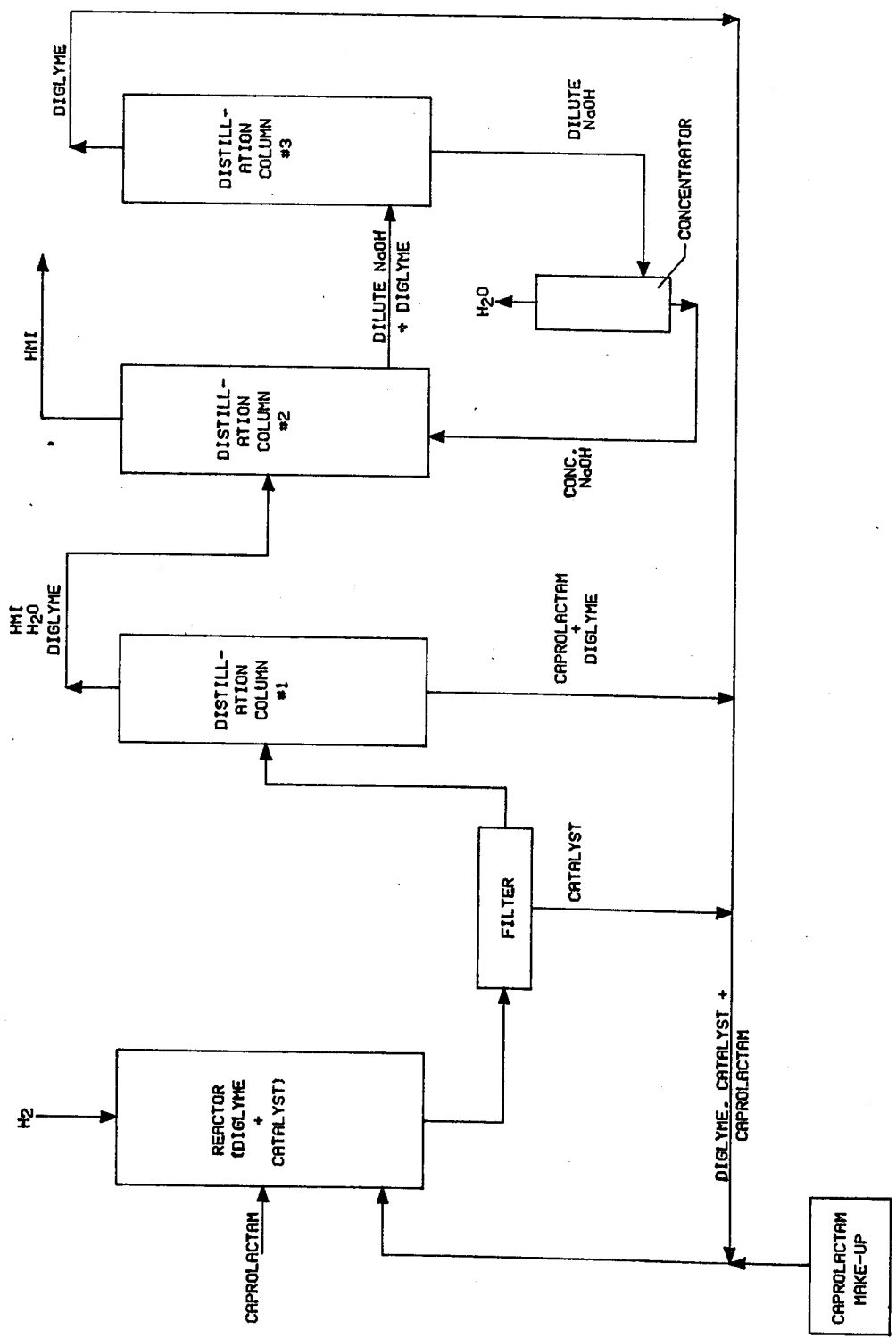

PRODUCTION OF HEXAMETHYLENEIMINE FROM CAPROLACTAM

BACKGROUND OF THE INVENTION

1. FIELD OF THE INVENTION

This invention relates to the production of hexamethyleneimine by the catalytic hydrogenation of ε-caprolactam.

2. DESCRIPTION OF THE PRIOR ART

Hexamethyleneimine, an intermediate used in the production of herbicides and insecticides, has heretofore been commercially produced as a by-product in the production of hexamethylenediamine, a nylon-6,6 monomer, in which either adiponitrile is reduced or 1,6-hexanediol is aminated. Such processes are indirect, low yield routes to hexamethyleneimine ("HMI"). It has previously been suggested to prepare HMI directly by the vapor phase reaction of oxepane and ammonia (U.S. Pat. No. 3,635,952 issued to Tyssee et al. in 1972) and by the vapor phase reaction of tetrahydropyran-2-methanol, hydrogen and ammonia (U.S. Pat. No. 3,635,951 issued to Tyssee et al. in 1972). However, such processes require the utilization of expensive and uncommon starting materials. It has also been heretofore suggested in U.S. Pat. No. 2,181,140 issued to Lazier et al. in 1939 to prepare HMI together with hexamethylenediamine by the catalytic hydrogenation of ε-caprolactam using Group VIII, Group IB or Group IIB metals as catalysts. The Lazier et al. patent is primarily directed to the production of hexamethyleediamine and although in the penultimate paragraph thereof it is broadly stated that by altering the hydrogenation conditions HMI can be obtained, such conditions are not disclosed.

SUMMARY OF THE INVENTION

In accordance with this invention, a method of preparing hexamethyleneimine is provided, which method comprises the steps of:

a. forming a solution of ε-caprolactam in a solvent selected from the group consisting of linear and cyclic ethers and polyethers having a boiling point of at least about 100° C., the solution having a concentration of about 1 to 40 percent by weight;

b. contacting said solution with gaseous hydrogen in the presence of a catalyst comprising copper chromite and at a temperature of about 150° to 300° C. and a pressure of at least about 1,000 psig, whereby a solution containing hexamethyleneimine is formed; and c. recovering hexamethyleneimine from said hexamethyleneimine-containing solution.

It has surprisingly been found that the choice of solvent, catalyst and temperature and pressure ranges are critical to this invention as the use of the other common solvents and catalysts or temperatures and pressures outside of the above ranges either fail to yield hexamethyleneimine or the yield is uneconomically low. Furthermore, the ε-caprolactam starting material is a commonly available compound used in the production of nylon-6. Moreover, it has been found that the HMI produced does not combine with the caprolactam to yield viscous polymeric materials and hence recycle is feasible and indeed beneficial. It has additionally been found that catalyst life is extensive and several recycle steps can be performed before the catalyst need be replenished.

BRIEF DESCRIPTION OF THE DRAWING

The sole FIGURE is a schematic flow sheet of the process of this invention wherein diglyme is employed as solvent and solvent, catalyst and caprolactam are recycled.

DESCRIPTION OF THE PREFERRED EMBODIMENTS

In accordance with the preferred embodiments of this invention, the ε-caprolactam (hereafter simply referred to as caprolactam) starting material contains less than about 0.1% water and is preferably anhydrous. This can be accomplished, for example, by subjecting the caprolactam to a distillation step. In addition, it has been found that certain impurities such as ε-aminocaproic acid, like water, have an adverse affect on the reduction reaction. Such impurities are preferably removed by fractional distillation of the caprolactam.

As mentioned above, the solvents which have been found effective for use herein are linear and cyclic ethers and polyethers having boiling points of at least about 100° C. These ethers include alkyl, cycloalkyl and aromatic mono-and polyethers of 2 to 20 carbon atoms. Among the linear ethers there can be employed ethers of the formula

$$R - O - [CH_2CH_2O]_n - R^1$$

wherein R and R¹ independently are selected from the group consisting of alkyl, alkenyl and aryl of 1 to 6 carbon atoms and n is an integer of 2 to 5. Exemplary of such ethers are diethylene glycol dimethyl ether (i.e., diglyme), diethylene glycol diethyl ether, diethylene glycol dipropyl ether, diethylene glycol dibutyl ether, bis[2-2(2-methoxy-ethoxy)ethyl] ether (i.e., tetraglyme) and the like. Other linear ethers include diaryl or dialkaryl ethers of 12-20 carbon atoms, such as diphenyl ether, benzyl ether and the like.

As cyclic ethers, there can be employed compounds having 5 or 6 members in the cyclic ring, such tetrahydrofuran, dioxolane, tetrahydropyran, 1,4 dioxane and trioxane.

The above ethers may be substitued with radicals that do not interfere with the reaction such as alkyl, alkylene and alkoxy of 1 to 6 carbon atoms, aryl, aralkyl and alkaryl of 6 to 10 carbon atoms and the like.

The above ethers have boiling points of at least about 100° C and preferably have boiling points above about 140° C. Ethers having boiling points below about 100° C have a high partial pressure under the present reaction conditions and thus adversely affect the reduction reaction. When ethers having boiling points above about 140° C are employed, separation of HMI (boiling point 138° C) from the reaction mass may readily be accomplished by stripping the product from the solvent.

Preferred solvents include diglyme, tetraglyme, dioxane and diphenyl ether; diglyme is especially preferred. Although in the following description reference is made to diglyme as the solvent, it is to be understood that other linear and cyclic ethers can be employed.

The caprolactam is dissolved in diglyme solvent to provide a concentration in the range of about 1 to 40% by weight, preferably about 10 to 20% by weight. Solubilization can be effected over a wide range of temperatures; the caprolactam may be in molten form and is dissolved in diglyme at a temperature of about 70° to 100° C. Alternately, the caprolactam may be in solid form and temperatures up to about its melting point (69° C.), preferably at about room temperature, may be employed during formation of the solution.

The caprolactam-diglyme solution is preferably prepared prior to charging into the reaction pressure vessel, although for batch reactions the solution can be prepared in the reaction vessel itself. The copper chromite catalyst, which is usually in powdered form, is preferably admixed with the solution but can alternatively be charged together with caprolactam and diglyme into the reaction vessel, especially for batch reactions.

As mentioned above, the catalyst comprises copper chromite. The copper chromite may contain additional minor amounts of other metals, preferably barium. On a weight basis, such barium-promoted copper chromite catalysts may contain from about 1 to 20% barium as the oxide. The catalyst is preferably employed in a finely divided form or alternatively may be deposited on a porous support such as diatomite, kielgelsuhr and the like. The catalyst is employed in a catalytic-promoting amount, which may range from about 0.5 to 15%, preferably about 1 to 10%, by weight, based on the combined weight of the caprolactam and diglyme.

Any suitable high pressure vessel may be employed for carrying out the reaction. Such chambers may be formed, for example, of stainless steel, titanium and the like; stainless steel is preferred. Autoclave reactors provided with heating and agitation devices are preferably employed.

The reaction mass containing caprolactam, diglyme, and copper chromite catalyst is heated to and maintain during reaction at a temperature in the range of about 150° to 300° C., preferably about 175° to 275° C. and most preferably about 185° to 215° C. At temperatures below about 150° C., the yield is substantially reduced and significant amounts of caprolactam are lost, whereas at temperatures above about 300° C., the yield is also reduced and no caprolactam is found in the reaction mixture which severely limits recycling. Hydrogen gas, preferably anhydrous, is introduced into the reaction vessel and is preferably introduced directly into the reaction solution. For example, the gas may be introduced at the bottom of the reactor through a diffuser. The pressure during reaction must be at least about 1,000 psig and may range up to about 4,000 psig or higher; preferably, the pressure is in the range of about 2,000 to 3,5000 psig and most preferably about 2000 to 2500 psig. Although pressures higher than about 4,000 psig may be employed, special type reactors are usually required and it may be found that higher pressures do not materially increase the product yield.

Preferably, the reaction mass is agitated during the reaction by means of a driven impellor and/or baffle and the like. The reaction is continued for a suitable period of time which may typically range, for example, from about ½ to 6 hours, preferably about 2 to 4 hours. After the reaction is completed, a solution containing HMI and water as reaction products, in addition to caprolactam, diglyme and by-products is formed. HMI may be recovered from this solution by any suitable process. Preferably, HMI is stripped from the solution since it is the low boiling organic component of the solution. For example, the reaction mixture may first be filtered to remove the catalyst and distilled through a distillation column where HMI, water and some diglyme are removed as overhead and caprolactam and the remaining diglyme are removed as bottoms. The HMI may be separated from the water and the diglyme by distillation in the presence of, for example, an alkali solution, such as a concentrated sodium hydroxide solution. The diglyme may be separated from the resultant dilute sodium hydrxiode solution by another distillation step and is preferably recycled to the reactor. The caprolactam and diglyme separated in the first distillation column are likewise preferably recycled, as is the catalyst which has been filtered out. Additional caprolactam is introduced into the recycle stream to provide the requisite concentration in the reactor. Concentrated sodium hydroxide may be recovered from the dilute solution by means of a concentrator and the concentrated solution recycled to the HMI distillation column.

It has been found that under the above reaction conditions, yields of HMI range up to about 95% and higher, with conversions of caprolactam up to about 60% and higher. The solvent, caprolactam and catalyst can be recycled many time without additional catalyst being added and at acceptable conversion rates. Thus, a continuous recycled process is very practical.

With reference to the drawing, a continuous recycle process is shown using diglyme as solvent. Caprolactam and hydrogen are fed to the reactor which contains sufficient diglyme and catalyst. Following the reaction, the catalyst is filtered off and recycled and the filtrate distilled in a first distillation column which yields HMI, water and some diglyme as overheads and caprolactam and diglyme as bottoms. The bottoms are recycled to the reactor and the overheads are fed to a second distillation column wherein concentrated sodium hydroxide is added to the mixture. HMI is recovered as the overhead and the bottoms, which contain dilute sodium hydroxide and diglyme, are fed to a third distillation column where diglyme is separated and recycled and the dilute sodium hydroxide is fed to a concentrator wherein water is removed. The resulting concentrated sodium hydroxide is recycled to the second distillation column. Additional caprolactam make-up is added as necessary. When necessary, the catalyst can be regenerated by caustic and/or steam treatments and the like.

It has been found that solvents other than those described above cannot be employed either because no HMI is obtained or the yield is too low. In addition, the reaction does not occur in the neat (i.e., caprolactam as solvent) or with HMI as solvent.

The following non-limiting examples further describe the present invention. All parts and percentages are by weight unless otherwise indicated.

EXAMPLE 1

A mixture of 90 parts of diglyme, 10 parts of caprolactam and 10 parts of copper chromite catalyst (analyzing as 51% by weight CuO and 47% by weight $Cr_2O_3$) was charged into a 300cc Autoclave Engineers Model ABP-300 stainless steel autoclave reactor provided with an impellor and baffle. The mass was heated to 200° C with agitation as hydrogen was introduced through a diffuser located near the bottom of the reactor at a rate sufficient to maintain a pressure of 2,200 psig for 2 hours. The reactor was then cooled down to 80° C. and samples were taken for gas chromatographic analysis. The product was identified as HMI. A conversion of 48% caprolactam to HMI was obtained.

EXAMPLE 2

This example shows the effect of catalyst concentration on caprolactam reduction. Following the procedure of Example 1, the reaction was condensed using the same catalyst as was employed in Example 1 at concentrations ranging from about 1 to 10% by weight based on the combined weight of solvent and caprolactam. The results are shown in Table 1.

Table 1

| Run No. | Concentration Percent | Catalyst Percent | Reaction Time Hours | Temp. °C. | Pressure psig | Conversion Percent |
|---|---|---|---|---|---|---|
| 1 | 10 | 10 | 2 | 200 | 2200 | 48 |
| 2 | 10 | 5 | 2 | 200 | 2500 | 45 |
| 3 | 10 | 2 | 2 | 200 | 3300 | 35 |
| 4 | 11.4 | 0.98 | 2 | 200 | 3400 | 17 |
| 5 | 10.4 | 10 | 2 | 200 | 3200 | 53 |

As can be seen from Table 1, even at low concentration of about 1% by weight catalyst, a conversion of about 17% is effected. At higher concentrations up to about 10% catalyst, a conversion rate of about 50% is obtained (Runs 1 and 5)

EXAMPLE 3

The purpose of this Example is to show the effect of temperature on caprolactam reduction. Example 1 was repeated and temperatures ranging from about 130° C to 270° C. were employed. The results are shown in Table 2.

Table 2

| Run No. | Concentration Percent | Catalyst Percent | Reaction Time Hours | Temp. °C. | Pressure psig | Conversion Percent |
|---|---|---|---|---|---|---|
| 1 | 10.4 | 4.98 | 2 | 200 | 3500 | 45 |
| 2 | 9.8 | 4.82 | 2 | 270 | 2900 | 28* |
| 3 | 10.1 | 4.86 | 2 | 130 | 2900 | 7** |

*No caprolactam found in reaction mixture.
**Loss of caprolactam of 20% of caprolactam charged.

As can be seen from Table 2, a temperature of 130° C. (Run 3) is unsuitable since loss of caprolactam amounted to about 20% of the caprolactam charged and the conversion rate was only 7%. A temperature of about 270° C. (Run 2) is marginally effective for commercial production since although a conversion rate in the range of 28% was obtained, no caprolactam was found in the reaction mixture, thus foreclosing the availability of recycling.

EXAMPLE 4

The purpose of this Example is to show the effect of pressure on the reduction of caprolactam. Example 1 was repeated with the pressure ranging from about 1,200 to 3,200 psig. The results are shown in Table 3.

Table 3

| Run No. | Concentration Percent | Catalyst Percent | Reaction Time Hours | Temp. °C. | Pressure psig | Conversion Percent |
|---|---|---|---|---|---|---|
| 1 | 10 | 10 | 2 | 200 | 2200 | 48 |
| 2 | 10.4 | 9.96 | 2 | 200 | 3200 | 53 |
| 3 | 10.2 | 4.99 | 2 | 200 | 1200 | 12 |
| 4 | * | * | 2 | 200 | 2900 | 35 |

*Continued from Run 3

As can be seen from Table 3, a pressure of 1200 psig (Run 3) provides a conversion rate of only about 12%. Pressures in the range of 2200 to 3200 psig (Runs 1 and 2) provide conversion rates of about 50%. It can be seen by comparing Runs 1 and 2 that increasing the pressure to 3200 psig from 2200 psig does not materially increase the conversion percentage.

EXAMPLE 5

This Example shows the effect the reduction time on the percent conversion. Example 1 was repeated with reaction times ranging from 1 to 4 hours. The results are shown in Table 4.

Table 4

| Run No. | Concentration Percent | Catalyst Percent | Reaction Time Hours | Temp. °C. | Pressure psig | Conversion Percent |
|---|---|---|---|---|---|---|
| 1 | 20 | 10 | 4 | 200 | 2600 | 36 |
| 2 | 20 | 10 | 3-½ | 200 | 2350 | 35 |
| 3 | 10 | 5 | 2 | 200 | 2350 | 38 |
| 4 | 10 | 5 | 1 | 200 | 2250 | 24 |

Table 4 shows that reaction times of about 1 hour can be employed with a conversion rate of about 24% but the reaction times in the range of 2 to 4 hours are more preferable and result in conversion percentages in the range of 35 to 40 percent.

EXAMPLE 6

The purpose of this example is to compare the catalytic activity of three types of copper chromite catalysts, as identified in Table 5. Example 1 was repeated using a temperature of 200° C. and pressures in the range of 2400 to 2480 psig. The results are shown in Table 5.

Table 5

| Run No. | Concentration Percent | Catalyst Percent | Reaction Time Hours | Temp. °C. | Pressure psig | Conversion Percent |
|---|---|---|---|---|---|---|
| 1 | 20 | 10 (a) | 4½ | 200 | 2480 | 37 |
| 2 | 20 | 10 (b) | 4 | 200 | 2450 | 20 |
| 3 | 20 | 10 (c) | 3½ | 200 | 2400 | 35 |

(a) - Cu-1106p copper chromite catalyst from Harshaw Chemicals; 39% CuO, 44% $Cr_2O_3$, 10% BaO.
(b) - Cu-0202p copper chromite catalyst from Harshaw Chemicals; 82% CuO, 17% $Cr_2O_3$.
(c) - Cu-1800p copper chromite catalyst from Harshaw Chemicals; 51% CuO, 47% $Cr_2O_3$.

As can be seen from Table 5, the copper chromite catalyst analyzing at 39% and 51%, by weight, copper oxide (Runs 1 and 3, respectively) were superior to the 82% CuO copper chromite (Run 2). However, the use of 82% CuO copper chromite still provides an acceptable amount of conversion.

EXAMPLE 7

This example demonstrates the long useful life of the catalysts. Example 1 was repeated and the catalyst was filtered and used for a recycled run. The operation was repeated four times. The results are shown in Table 6.

Table 6

| Run No. | Concentration Percent | Catalyst Percent | Reaction Time Hours | Temp. °C. | Pressure psig | Conversion Percent |
|---|---|---|---|---|---|---|
| 1 | 10 | 5 | 2 | 200 | 3600 | 45 |
| 2 | 10 | From Run 1 | 2 | 200 | 3650 | 39 |
| 3 | 10 | From Run 2 | 2 | 200 | 3650 | 38 |
| 4 | 10 | From Run 3 | 2 | 200 | 3600 | 29 |
| 5 | 10 | From Run 4 | 2 | 200 | 3450 | 28 |

As can be seen from Table 6, the catalyst can be recycled 4 times and during the fifth run the conversion rate was an acceptable 28%.

EXAMPLE 8

The purpose of this Example is to show the effect of recycling of catalyst, solvent and unreacted caprolactam on the reduction of caprolactam. The recycling was accomplished by distilling off HMI and water (and subsequently recovering HMI by distillation) and recycling catalyst, solvent and unreacted caprolactam with appropriate caprolactam make-up. The results are shown in Table 7.

As can be seen from Table 7, it is feasible to recycle catalyst, solvent and unreacted caprolactam with high levels of conversions.

EXAMPLE 9

This example shows the utilization of tetraglyme as solvent. Example 1 was repeated except that 80 parts of tetraglyme, 25 parts of caprolactam and 10 parts of barium-promoted copper chromite catalyst (catalyst a of Table 5) were charged to the reactor. Reactions conditions were 200° C and 2600 psig for 4 hours. A conversion of 16.1% to HMI was obtained.

EXAMPLE 10

Example 10 was repeated using 80 parts tetraglyme, 20 parts caprolactam and 10 parts of copper chromite catalyst (catalyst b from Table 5) and reaction conditions of 200° C and 2500 psig for 4 hours. A conversion of 22.4% to HMI was obtained.

Examples 9 and 10 demonstrate that tetraglyme is an effective solvent; conversions to HMI, however, are lower with tetraglyme at the same reaction conditions than with diglyme.

EXAMPLES 11 and 12

These examples show the utilization of 1,4 dioxane as solvent. In Example 11, Example 1 was repeated with 100 parts dioxane, 20 parts caprolactam and 10 parts copper chromite catalyst (catalyst a of Table 5) at 250° C and 3200 psig for 2 hours. The percent conversion to Table 7

| Run No. | Concentration Percent | Catalyst Percent | Reaction Time Hours | Temp. °C. | Pressure psig | Conversion Percent |
|---|---|---|---|---|---|---|
| 1 | 9.7 | 4.87 (a) | 2 | 200 | 2800 | 41 |
| 2 | (Recycled from previous run + make-up) | From previous run | " | " | " | 38 |
| 3 | " | " | " | " | " | 38 |
| 4 | " | " | " | " | " | 32 |
| 5 | " | " | " | " | " | 31 |
| 6 | " | " | " | " | " | 30 |
| 7 | 10.2 | 4.95 (b) | " | " | 3450 | 44 |
| 8 | (Recycled from previous run + make up) | From previous run | " | " | 3370 | 33 |
| 9 | " | " | " | " | 3325 | 26 |
| 10 | " | " | " | " | 2800 | 22 |

(a) - copper chromite containing 39% CuO, 44% $Cr_2O_3$ and 10% BaO
(b) - copper chromite containing 51% CuO and 47% $Cr_2O_3$ HMI was 34.2%. In Example 12, Example 11 was repeated except that catalyst c from Table 5 was employed and the pressure was 33 psig. The percent conversion to HMI was 32.5%. These examples demonstrate that dioxane is an effective solvent for carrying out the reaction.

EXAMPLE 13

This example shows the use of diphenyl ether as solvent. Example 10 was repeated except that diphenyl ether was substituted for tetraglyme and catalyst a of Table 5 was employed. Reaction conditions were 200° C and 3000 psig for 2 hours and the percent conversion to HMI was 18.5%. This example demonstrates that diphenyl ether is an effective solvent but is less effective than diglyme and dioxane.

EXAMPLES 14-17 (COMPARATIVE)

In these examples, the procedure of the foregoing examples was repeated using different solvents and no solvent. In Example 14, HMI was employed as solvent, no reduction of caprolactam was noted and the amount of HMI in the final reaction mass was less than that charged. In Example 15, the reaction was conducted in the neat; a polymeric mass was obtained and no reduction to HMI was noted. In Example 16, aqueous acetic acid was employed as solvent; no reduction to HMI was noted. In Example 17, glyme was employed as solvent and no reduction to HMI was noted.

EXAMPLES 18-20 (COMPARATIVE)

These examples demonstrate the ineffectiveness of other catalysts. Example 1 was repeated except with the catalysts and under the conditions listed in Table 8.

Table 8

|  | Example 18 | Example 19 | Example 20 |
|---|---|---|---|
| Solvent | none | dioxane | dioxane |
| Concentration, % | — | 16.7 | 16.7 |
| Catalyst | Raney nickel | Raney nickel | Raney cobalt |
| % Catalyst | 10 | 8.3 | 8.3 |
| Reaction time, hours | 2 | 4 | 4 |
| Temperature, °C | 200 to 250 | 200 | 150 |
| Pressure, psig | 150 to 1000 | 3300 | 3600 |
| Conversion % | 0 | 6.7 | 3.8 |

Table 8 shows that the utilization of Raney nickel and Raney cobalt catalysts results in no or very little conversion to HMI. In additional examples employing various solvents and reaction conditions, the following catalysts likewise showed no or negligible reduction of caprolactam to HMI; ruthenium on carbon, platinum oxide, palladium oxide, palladium, nickel, stabilized nickel on kieselguhr and Raney chromium promoted with active nickel.

EXAMPLE 21 (COMPARATIVE)

This example shows the effect of ε-aminocaproic acid impurity on the reduction of caprolactam to HMI. Run ε of Example 2 was repeated except that 1 part ε-aminocaproic acid was charged to the reactor. The conversion to HMI was only 9.1% versus 35% in Run 3 of Example 2. Hence, ε-aminocaproic acid (the hydrolysis product of caprolactam) inhibits the reduction reaction.

It is to be understood that variations and modifications of the present invention may be made without departing from the scope of the invention. It is also to be understood that the scope of the invention is not to be interpreted or limited to the specific embodiments disclosed herein but only in accordance with the appended claims when read in light of the foregoing disclosure.

We claim:
1. A method of preparing hexamethyleneimime which comprises the steps of:
   a. forming a solution of ε-caprolactam in a solvent selected from the group consisting of linear and cyclic ethers and polyethers having a boiling point of at least about 100° C., said solution having a concentration of about 1 to 40 percent by weight;
   b. contacting said solution with gaseous hydrogen in the presence of a catalyst comprising copper chromite and at a temperature of about 185° to 215° C. and a pressure of at least about 1,000 psig, whereby a solution containing hexamethyleneimine is formed; and
   c. recovering hexamethyleneimine from said hexamethyleneimine-containing solution.

2. The method of claim 1 wherein said solvent is selected from the group consisting of alkyl, cycloalkyl and aromatic mono- and polyethers of 2 to 20 carbon atoms.

3. The method of claim 1 wherein said solvent is selected from compounds of the formula $$R - O - [CH_2CH_2O]_n - R^1$$

wherein R and $R^1$ independently are alkyl, alkenyl or aryl of 1 to 6 carbon atoms and n is an integer of 2 to 5.

4. The method of claim 3 wherein said ether is diglyme.

5. The method of claim 1 wherein said solvent is selected from the group consisting of cyclic ethers having 5 or 6 members in the cyclic ring.

6. The method of claim 1 wherein said solvent is selected from the group consisting of diglyme, tetraglyme, dioxane and diphenyl ether.

7. The method of claim 1 wherein said concentration is in the range of about 10 to 20 percent by weight.

8. The method of claim 1 wherein said caprolactam is treated prior to step (a) to remove water and ε-aminocaproic acid.

9. The method of claim 1 wherein said hexamethyleneimine is stripped from said hexamethyleneimine-containing solution by distillation.

10. The method of claim 1 wherein said pressure is in the range of about 2000 to 3500 psig.

11. The method of claim 10 wherein said pressure is in the range of about 2000 to 2500 psig.

12. The method of claim 1 wherein said catalyst is employed in a concentration of about 1 to 10 percent by weight based on the combined weight of solvent and caprolactam.

13. The method of claim 1 wherein said catalyst contains barium.

14. The method of claim 1 wherein said caprolactam is distilled prior to step (a) to remove impurities therein.

15. The method of claim 4 wherein said pressure is in the range of about 2000 to 2500 psig.

16. The method of claim 1 wherein said method is a continuous method and caprolactam, solvent and catalyst are recycled to step (b).

17. The method of claim 15 wherein said catalyst concentration is in the range of about 1 to 10 percent by weight based on the combined weight of solvent and caprolactam.

18. The method of claim 16 wherein said solvent is diglyme, wherein prior to step (c), said catalyst is removed from said hexamethyleneimine — containing solution, wherein step (c) comprises (1) distilling said solution whereby an overhead product containing hexamethyleneimine and water and a bottoms product containing caprolactam and diglyme are obtained, (2) distilling said overhead product in a second distillation step wherein hexamethyleneimine is separated from water, and wherein said bottoms product is recycled to step (b) together with sufficient caprolactam make-up to provide a solution of said concentration of caprolactam.

19. The method of claim 18 wherein a concentrated solution of sodium hydroxide is fed to said second distillation step whereby hexamethyleneimine is obtained as overhead and a dilute sodium hydroxide solution is obtained as bottoms, wherein said dilute sodium hydroxide solution is subject to a third distillation step whereby any diglyme present in said solution is obtained as overhead product and dilute sodium hydroxide is obtained as bottoms product, and wherein said diglyme obtained as bottoms product, and wherein said diglyme obtained as overhead product is recycled to step (b).

20. The method of claim 12 wherein said dilute sodium hydroxide bottoms product from said third distillation step is concentrated and the resulting concentrated solution is recycled to said second distillation step.

* * * * *